US006589544B2

(12) United States Patent
Leong

(10) Patent No.: US 6,589,544 B2
(45) Date of Patent: Jul. 8, 2003

(54) ALOE VERA IMPREGNATED ELASTOMERIC ARTICLE AND METHOD OF MANUFACTURE

(75) Inventor: Ronald Low Pew Leong, Kuala Lumpur (MY)

(73) Assignee: Matang Manufacturing Sdn. Bhd., Kuala Lampur (MY)

( * ) Notice: Subject to any disclaimer, the term of this patent is extended or adjusted under 35 U.S.C. 154(b) by 0 days.

(21) Appl. No.: 09/923,805

(22) Filed: Aug. 7, 2001

(65) Prior Publication Data

US 2002/0114825 A1 Aug. 22, 2002

(30) Foreign Application Priority Data

Dec. 21, 2000 (MY) .................................. PI 20006032

(51) Int. Cl.⁷ .......................... A61K 9/00; A41D 19/00; A61F 5/44
(52) U.S. Cl. .......................... 424/402; 424/400; 2/159; 2/163; 2/168; 604/349
(58) Field of Search .................. 424/402, 404, 424/408; 604/349, 159, 163, 168

(56) References Cited

U.S. PATENT DOCUMENTS

| | | | |
|---|---|---|---|
| 4,178,372 A | * | 12/1979 | Coats |
| 4,310,928 A | | 1/1982 | Joung |
| 5,326,515 A | * | 7/1994 | Sakaki et al. |
| 5,335,373 A | | 8/1994 | Dangman et al. |
| 5,357,636 A | | 10/1994 | Dresdner, Jr. et al. |
| 5,869,072 A | | 2/1999 | Berry |
| 5,993,972 A | | 11/1999 | Reich et al. |
| 6,087,310 A | | 7/2000 | Henkel |
| 6,274,154 B1 | * | 8/2001 | Chou |

FOREIGN PATENT DOCUMENTS

| | | | |
|---|---|---|---|
| JP | 411229211 A | * | 8/1999 |
| WO | WO93/18745 | | 9/1993 |
| WO | WO00/59450 | | 10/2000 |
| WO | WO00/65911 | | 11/2000 |

* cited by examiner

Primary Examiner—Gollamudi S. Kishore
Assistant Examiner—Simon J. Oh
(74) Attorney, Agent, or Firm—Merchant & Gould P.C.

(57) ABSTRACT

In a method for manufacturing a thin-walled, skin-contacting elastomeric article to be worn over a human body part, an article-shaped form is dipped into a latex composition that has been mixed with the extract of the plant *Aloe vera* forming the article. The article is processed and cured so that the extract is present within the article as one or combination of a polymer, co-polymer and filler of the article. An *Aloe vera* coating may be applied to at least one surface of the article.

16 Claims, No Drawings

US 6,589,544 B2

ALOE VERA IMPREGNATED ELASTOMERIC ARTICLE AND METHOD OF MANUFACTURE

FIELD OF THE INVENTION

This invention relates to polymeric products and the method for making the same. In particular, this invention concerns thin-walled elastomeric articles including gloves, condoms, masks, finger cots and like products. The method of manufacturing such articles is also disclosed.

BACKGROUND

Elastomeric articles such as gloves and condoms are designed to be worn skin tight, but this required fit often results in discomfort to the wearer, particularly when the article is worn for extended periods of time. The industry has attempted to increase wearing comfort and convenience of the articles by coating the skin-contacting surface with lotions or powders, resulting in undesirable residues on the skin. Hence, there is a need for a new type of elastomeric article, which combines the qualities of thinness, durability, ease of use and comfort.

Aloe vera, the gelatinous substance extracted from Aloe plants, has been known for centuries for its useful therapeutic properties. It has been used extensively in a wide range of beauty products, such as cosmetics, soaps, and lotions. However, its use in the production of mass manufactured articles designed to be worn against the skin, particularly elastomeric articles such as gloves, condoms, masks, finger cots and like articles, is little if at all known, as discussed in the following closest prior art.

U.S. Pat. No. 6,087,310 (Henkel) discloses a polymer latex composition for use in cleaning hands and skin without use of water or rinsing. The latex emulsion of this patent includes plant extracts such as Aloe vera and other plant or botanical extracts such as Jojoba oil, wheat germ extract, corn huskers lotion, and vegetable oil in general. The latex formulation is not used in forming rubber articles or for vulcanisation to produce cured or vulcanised elastomeric products. It is used solely as a rinse-free hand-cleaning or washing liquid.

U.S. Pat. No. 5,993,972 (Reich, et. al.) concerns admixing hydrophilic and hydrophobic diols in certain ratios to produce polyurethanes. It includes a preferred embodiment where filler is added to the composition to produce elastomeric (both natural and synthetic rubber) gloves, including exam, surgical, industrial, medical and clean room gloves. Several categories of additives are mentioned that may be added to the polymer solution for forming the gloves. One of the categories of additive—oil, is mentioned to include corn oil, sesame oil, sweet almond oil, hydrogenated vegetable oil, apricot oil, olive oil and starch. Vegetable sterols are also mentioned as stabilisers for the mixture. No specific mention of Aloe vera being used was found. It should be noted that the plant-based substances are used as additive or stabilisers and not as a polymer, co-polymer or filler of the resultant polymeric product.

U.S. Pat. No. 4,310,928 (Joung) discloses a talc-free glove which is achieved by providing a lipo compound coating on the glove surface with a surfactant therefor. The lipo compound includes vegetable oils. The coating and surfactant are cured at temperatures of 260° F. Again, there is no mention of Aloe vera per se.

In U.S. Pat. No. 5,869,072 (Berry), Aloe vera is used as a moisturising substance to be delivered to a therapeutic glove for the treatment of dry hands. It is not used in the process and for the manufacture of the glove itself.

In the wake of the scare of AIDS infecting medical personnel through broken surgical gloves, U.S. Pat. No. 5,335,373 (Dangman, et. al.) and U.S. Pat. No. 5,357,636 (Dresdner, Jr., et. al.) both proposes double-layer gloves wherein a thin space is provided between the inner and outer layers which is filled with non-liquid antiseptic compositions. The breach in the glove wall causes the antiseptic compositions to be spilled out thus disinfecting the affected area. Plant oils including Jojoba oil have been suggested only as emulsifiers. There is no mention of Aloe vera.

The industry has yet to successfully increased the comfort of an article designed to be worn against the skin by incorporating Aloe vera into a latex composition to produce cured and vulcanized elastomeric products in which the Aloe vera is part of the substrate of the product, thus providing its moisturizing and other therapeutic properties integrally with substrate itself.

SUMMARY OF INVENTION

The present invention is an article of manufacture comprising a thin-walled elastomeric article to be worn against the skin and the method of making the same. The method of manufacture comprises mixing Aloe vera extract and a latex composition to create a dipping mix, dipping a form into the mix to coat the form with the dipping mix and forming the article. The article is then cured and processed so that the extract is present as at least one of a polymer, co-polymer and filler within the article. The finished article is then removed from the form.

In one preferred embodiment of the invention, the article is further coated with at least one layer of Aloe vera on the skin-contacting surface. Preferably, the Aloe vera coating further comprises at least one suitable preservative in an aqueous solution.

In another preferred embodiment of the invention, the article contains about 15% to about 20% Aloe vera extract by weight in 1:1 concentrate or equivalent concentration. Preferably, the amount of Aloe vera extract is about 15%.

In yet another preferred embodiment, the article may be manufactured by dipping a form into a latex composition comprising not more than about 15 kg Aloe vera extract mixed with about every 100 kg of the latex composition.

In still another preferred embodiment, about 1.125 kg of the Aloe vera extract in 200:1 concentrate is mixed with about every 100 kg of natural rubber total solids in an aqueous latex composition to produce finished articles containing the equivalent of about 15% Aloe vera extract in 1:1 concentrate.

Accordingly, it is an object of the present invention to provide an elastomeric article whose substrate is impregnated with Aloe vera extract to give the article moisturizing properties.

Another object of the present invention is to provide for a thin-walled elastomeric article of natural rubber substrate in which Aloe vera extract is composited therewith as a polymer, co-polymer and filler of the article such that the emollient properties of the extract are incorporated into the article's substrate.

A further object of the present invention is to provide for a method for the manufacture of the aforesaid articles.

Many other objects and features of the present invention will be obvious to those of skill in the art upon contemplation of the disclosure herein.

DETAILED DESCRIPTION

The present invention is an article of manufacture comprising a thin-walled elastomeric article to be worn against the skin and the method of making the same. The method of manufacture comprises mixing *Aloe vera* extract and a latex composition to create a dipping mix, dipping a form into the mix to coat the form with the dipping mix and forming the article. The article is cured and processed so that the extract is present as at least one of a polymer, co-polymer and filler within the article. The finished article is then removed from the form.

In the finished article, the *Aloe vera* extract may be expected to permeate or impregnate the substrate as the latex-*Aloe vera* extract composition is vulcanized and cured. Hence, the emollient and other therapeutic properties of *Aloe vera* are provided integrally with the article.

The types of articles which may be advantageously manufactured using this method are thin-walled elastomeric products designed for skin touching or to be worn skin tight, such as gloves, condoms, finger cots, masks, etc. The cross-sectional diameter of the finished articles may vary according to the particular article's function, but ideally should be no less than about 0.08 cm thick. Thinner articles may be made, but with decreased durability of the substrate. Our experience is that incorporation of *Aloe vera* and its unique properties integrally in the substrate of an article results in a product that is more comfortable to wear as well as convenient to use when compared to elastomeric products currently available.

In one preferred embodiment, the article manufactured according to the process of the present invention may be further coated with one or more layers of *Aloe vera* extract at least on the skin-contacting surface. The further coat may be achieved by dipping the article into an *Aloe vera* extract solution, for example, according to the following formulation:

| | |
|---|---|
| Aloe vera extract (1:1 concentrate) | 20% to 30% |
| Sodium benzoate (preservative) | 0.025% to 0.075% |
| Potassium sorbate (preservative) | 0.025% to 0.075% |
| Water | 70% to 80%. |

It would be appreciated by a person skilled in the art that the preservative used may be substituted with any other suitable preservative for plant materials in an aqueous solution apart from benzoate and sorbate.

*Aloe vera* extract is available commercially most commonly in dried concentrate or powder form in various concentration relative to 1:1 which is 1 part of *Aloe vera* extract for 1 part of the weight of the plant. For example, a batch of *Aloe vera* powder at 200:1 concentrate will need to be mixed with aqueous solution (for example water or rubber latex) to reduce it to 1:1 concentration for ease of mixing with latex composition or suitable for mixing into a dipping mix. It is preferred that the amount of *Aloe vera* mixed into the latex composition is sufficient for a form to be dipped thereinto, processed and cured to make an article containing about 15% to about 20% by weight of *Aloe vera* extract in 1:1 concentrate or equivalent concentration. Most preferably, the article contains about 15% by weight of *Aloe vera* extract in 1:1 concentrate.

In one example of preparing a latex composition mixed with *Aloe vera* extract, about 15 kg of the extract in 1:1 concentrate is mixed with about every 100 kg of the latex composition. The articles made therefrom have the preferred amount of the extract, i.e. about 15%.

A concentrated extract may be used, but less is required. In another example of preparing a latex composition mixed with *Aloe vera* extract, about 1.125 kg by weight of the extract in 200:1 concentrate is mixed with about every 100 kg of natural rubber total solids in an aqueous latex composition to produce a dipping mix. The articles made therefrom have the preferred amount of the extract, i.e. about 15% in 1:1 concentrate or equivalent.

It is understood by a person skilled in the art that the term "*Aloe vera* extract" employed in this specification comprises the composition of substances extracted principally from the parenchymatous tissue in the leaf center of the *Aloe vera* Linne (also known as *Aloe barbadensis* Miller, *Curacao aloe,* or *Barbados aloe*) in the form of mucilaginous gel known for its emollient and wound healing activity as described in Merck Index's Monographs no. 312 and 314. It is understood that the term "extract" covers the plurality of specific mucopolysaccharides compounds which may have been identified including aloin (Chemical Abstracts Service, CAS name: 10-Glucopyranosyl-1,8-dihydroxy-3-(hydroxymethyl)-9(10 H)-anthraceone), aloe-emodin, etc. or derivatives therefrom such as aloeresin (CAS name:(E)-3-(4-hydroxyphenyl)-2-propenoic acid 2-prime-ester with 8-beta-D-glucopyranosyl-7-hydroxy-5-methyl-2-(2-oxo propyl)-4H-1-benzopyran-4-one). It is further understood by those skilled in the art that this extract may include the latex of the plant and may contain varying amounts of aloin, aloe-emodin, chrysophanic acid, volatile oil, and resins. Hence, the term "extract" does not cover any specific compound or active ingredient of the plant.

It is also understood by a person skilled in the art that the term "latex composition" describes a substance in which natural rubber solids are mixed with various additives to form a mixture which can then be processed to form rubber. Those skilled in the art understand that the various additives which may be part of the latex composition impart properties such as color or fragrance to the finished article, and do not affect the method of manufacture and the unique properties of an article formed by the method of the present invention.

The specific compounds and substances previously described are not to be considered as departures from the meaning of the term "*Aloe vera* extract" or "latex composition" of the present invention as illustrated by the examples and specific embodiments described. Therefore, the spirit and scope of the appended claims should not be limited to the description of the preferred versions and examples contained herein.

What is claimed is:

1. A method of manufacturing a thin-walled skin-contacting elastomeric article to be worn over a human body part, the method comprising:
    (a) mixing an extract of an *Aloe vera* plant with a latex composition to create a dipping mix;
    (b) dipping an article-shaped form into the dipping mix to coat the form with the dipping mix forming the article;
    (c) curing and processing the article so that the extract is present as at least one of
        a polymer, copolymer and filler within the article; and
            further coating at least one surface of the article with
            at least one layer of the after curing the article.

2. The method of claim 1, wherein the *Aloe vera* extract is applied in an aqueous solution containing at least one suitable preservative.

3. A latex dipping mix for use in the method of claim 1, comprising an *Aloe vera* extract mixed with a latex composition, wherein the mix comprises about 15 kg to about 20 kg of the *Aloe vera* extract with about every 100 kg of the latex composition.

4. The dipping mix of claim 3, wherein the *Aloe vera* extract is mixed with the latex composition in amounts to produce an article having about 15% of the *Aloe vera* extract by weight.

5. The dipping mix of claim 3, wherein the mix comprises about 1.125 kg of the *Aloe vera* extract in a 200:1 concentration with about every 100 kg of natural rubber solids.

6. The dipping mix of claim 3, wherein the mix contains not more than 15 kg of the *Aloe vera* extract for every 100 kg of the latex composition.

7. A thin-walled skin-contacting elastomeric article to be worn over a main body part, comprising:
   a shaped rubber substrate impregnated with an extract of an *Aloe vera* plant, the extract being present as at least one of a polymer, copolymer and filler within the substrate,
   a coating consisting essentially of an extract of an *Aloe vera* plant, the coating being disposed on at least one surface of the substrate.

8. The article of claim 7, wherein the article has at least one wall having a cross-sectional diameter of about at least 0.08 cm.

9. The article of claim 7, wherein the substrate is selected from the group consisting of a glove, condom, finger cot, or face mask.

10. The article of claim 7, wherein the coating is applied using an aqueous solution containing at least one suitable preservative.

11. The article of claim 7, wherein the article contains about 15% to about 20% by weight of the *Aloe vera* extract.

12. The article of claim 7, wherein the article contains about 15% by weight of *Aloe vera* extract.

13. A method according to claim 1, wherein the further coating is applied by dipping the article into a solution of *Aloe vera* extract in 1:1 concentrate at 15% to 30% by weight concentration.

14. A method according to claim 13 wherein the concentration is 15% by weight.

15. The method of claim 2, wherein the at least one surface of the article is the skin contacting surface.

16. The article of claim 7, wherein the coating consisting essentially of an extract of an *Aloe vera* plant is disposed on a skin contacting surface.

\* \* \* \* \*

UNITED STATES PATENT AND TRADEMARK OFFICE
CERTIFICATE OF CORRECTION

PATENT NO. : 6,589,544 B2
DATED : July 8, 2003
INVENTOR(S) : Leong

It is certified that error appears in the above-identified patent and that said Letters Patent is hereby corrected as shown below:

Column 4,
Line 64, "of the after curing" should read -- of a coating consisting essentially of an extract of an *Aloe vera* plant after curing --

Column 5,
Line 17, "main body part," should read -- human body part, --

Column 6,
Line 12, "of *Aloe vera* extract." should read -- of the *Aloe vera* extract. --
Line 19, "claim 2," should read -- claim 1, --

Signed and Sealed this

Second Day of December, 2003

JAMES E. ROGAN
*Director of the United States Patent and Trademark Office*